United States Patent
Smith

(10) Patent No.: US 10,238,759 B2
(45) Date of Patent: Mar. 26, 2019

(54) POWER SUPPLY CONNECTOR FOR A SUBMERSIBLE PUMP AND LIGHT SOURCE

(71) Applicant: Phoenix Environmental, Inc., Plymouth, MI (US)

(72) Inventor: Casey Joe Smith, Scottsdale, AZ (US)

(73) Assignee: PHOENIX ENVIRONMENTAL, INC., Plymouth, MI (US)

( * ) Notice: Subject to any disclaimer, the term of this patent is extended or adjusted under 35 U.S.C. 154(b) by 137 days.

(21) Appl. No.: 15/154,091

(22) Filed: May 13, 2016

(65) Prior Publication Data
US 2016/0331856 A1    Nov. 17, 2016

Related U.S. Application Data

(60) Provisional application No. 62/160,724, filed on May 13, 2015.

(51) Int. Cl.
*A61L 2/10*   (2006.01)

(52) U.S. Cl.
CPC ...................... *A61L 2/10* (2013.01)

(58) Field of Classification Search
CPC ......................................................... A61L 2/10
See application file for complete search history.

(56) References Cited

U.S. PATENT DOCUMENTS

| | | | |
|---|---|---|---|
| 5,553,794 A * | 9/1996 | Oliver | E03F 5/22 137/386 |
| 5,664,696 A * | 9/1997 | Canga | B65D 90/24 220/23.4 |
| 2005/0061743 A1* | 3/2005 | Buttner | A61L 2/0011 210/646 |
| 2013/0323128 A1* | 12/2013 | Owen | A61L 9/205 422/121 |

FOREIGN PATENT DOCUMENTS

EP        2319545 A1 *   5/2011   .............. A61L 2/10

* cited by examiner

*Primary Examiner* — Kevin Joyner
(74) *Attorney, Agent, or Firm* — Cantor Colburn LLP

(57) ABSTRACT

A method of supplying power to a storage tank, can include attaching a power supply connector to a submersible pump wherein the power supply connector is dispersed between a pump motor and a pump head or wherein the power supply connector is dispersed above the pump head, wherein the submersible pump is located within a storage tank, wherein the storage tank comprises a decontamination region containing fuel and an ultraviolet light source located in the decontamination region; supplying power to the pump motor, wherein the pump motor power simultaneously supplies power to the ultraviolet light source; and irradiating the fuel with the ultraviolet light.

18 Claims, 5 Drawing Sheets

US 10,238,759 B2

POWER SUPPLY CONNECTOR FOR A SUBMERSIBLE PUMP AND LIGHT SOURCE

BACKGROUND

To protect public health and the environment, the United States Environmental Protection Agency Clean Air Highway Diesel final rule stipulated a 97% reduction in sulfur content of highway diesel fuel beginning in June 2006. Accordingly, diesel fuel, for use in locomotives, marine vessels, and in automotive vehicles, was altered so that the sulfur content was reduced from 500 parts per million (ppm) in low sulfur diesel to 15 ppm, referred to as ultra-low sulfur diesel.

From as early as 2007, the Petroleum Equipment Institute started receiving reports of unusually severe and accelerated corrosion of both fiberglass and metal parts associated with storage tanks and equipment used for dispensing, transporting, and storing ultra-low sulfur diesel. Reports included, for example, observations of a metallic coffee ground type substance clogging the dispenser filters and of corrosion and/or malfunctioning of seals, gaskets, tanks, meters, leak detectors, solenoid valves, and riser pipes.

The presence of acetic acid in high concentration in the vapor sampled from various ultra-low sulfur diesel containing tanks, as well as the concentration of acetate in the water bottoms, suggest that acetic acid may be reacting with the iron to produce the scale and corrosion observed of the corroded equipment. As such, it is believed that the corrosion ultimately arises from increased levels of acetic acid in the ultra-low sulfur diesel, where the acetic acid is likely being produced by acetic acid producing bacteria feeding on low levels of ethanol contamination, possibly by the following reaction:

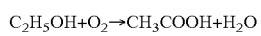

$$C_2H_5OH + O_2 \rightarrow CH_3COOH + H_2O$$

It was found that fuel comprising even as little as 0.0033 volume percent of ethanol in the presence of enough bacteria and oxygen could result in high enough amounts of acetic acid to cause extensive corrosion.

Acetic acid producing bacteria is likely to be the cause of the increased levels of acetic acid as bacteria of the family Acetobacteraceae was found to be present in the bottom water and/or in the sediment that accumulates in, for example, the storage tanks. Bacteria of the family Acetobacteraceae, specifically of the genus *Acetobacter*, are known to metabolize ethanol into acetic acid in the presence of oxygen and water in slightly acidic conditions. It is believed that higher levels of acetic acid producing bacteria are present in ultra-low sulfur diesel as compared to low sulfur diesel due to the higher levels of sulfur functioning as a natural biocide in the low sulfur diesel.

A system and method for reducing the amount of acetic acid producing bacteria is therefore desirable in order to reduce the levels of acetic acid and to ultimately reduce the amount of corrosion of the equipment used in the storage and transport of fuel.

BRIEF DESCRIPTION

The above described and other features are exemplified by the following figures and detailed description.

A method of supplying power to a storage tank, comprises: attaching a power supply connector to a submersible pump, wherein the power supply connector is dispersed between a pump motor and a pump head or wherein the power supply connector is dispersed above the pump head, wherein the submersible pump is located within a storage tank, wherein the storage tank comprises a decontamination region containing fuel and an ultraviolet light source located in the decontamination region; supplying power to the pump motor, wherein the pump motor power simultaneously supplies power to the ultraviolet light source; and irradiating the fuel with the ultraviolet light.

A power supply connector for connecting a submersible pump and a light source, comprises: a submersible pump disposed within a storage tank; a power supply connector attached to a submersible pump wherein the power supply connector is dispersed between a pump motor and a pump head or wherein the power supply connector is dispersed above the pump head, wherein the power supply connector comprises a pin connector configured to attach the pump motor to the pump head or wherein the power supply connector comprises an adaptor configured to attach the pump motor to the pump head; wherein the power source includes direct current, alternating current, or a combination comprising at least one of the foregoing; and wherein the power source includes a power transformer capable of transforming from alternating current to direct current or from direct current to alternating current at various voltages.

A fuel decontamination unit, comprises: a power supply connector attached to a submersible pump wherein the power supply connector is dispersed between a pump motor and a pump head or wherein the power supply connector is dispersed above the pump head, wherein the submersible pump is located within a storage tank, wherein the storage tank comprises a decontamination region containing fuel and an ultraviolet light source located in the decontamination region; wherein the decontamination unit contains fuel and wherein the ultraviolet light is configured to irradiate the fuel

BRIEF DESCRIPTION OF THE DRAWINGS

Refer now to the figures, which are exemplary embodiments, and wherein the like elements are numbered alike.

DETAILED DESCRIPTION

Figure 1:
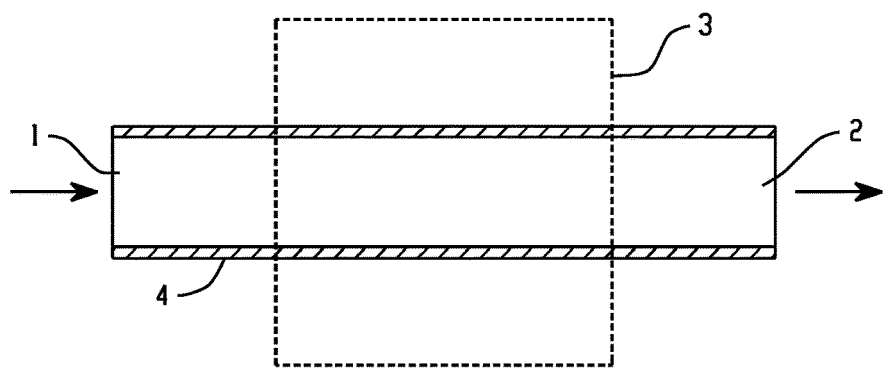
FIG. 1 illustrates a decontamination unit.

The switch to ultra-low sulfur diesel from low sulfur diesel has resulted in a dramatic increase in corrosion of the equipment that houses and transports the ultra-low sulfur diesel. It is believed that the increased corrosion is likely due to an increase in the level of acetic acid producing microorganisms, as there is less sulfur present in ultra-low sulfur diesel to act as a biocide for said microorganisms.

Disclosed herein is a method of supplying power to a storage tank containing a decontamination unit, a power supply connector for connecting power to the decontamination unit, and a decontamination unit containing the power supply connector. With such a method and units, the level of microorganisms in fuel such as fuel oil or diesel fuel including low sulfur diesel and ultra-low sulfur diesel can be reduced.

A method of supplying power to a storage tank, can include attaching a power supply connector to a submersible pump. The power supply connector can be dispersed between a pump motor and a pump head or the power supply connector can dispersed above the pump head. The submersible pump can be located within a storage tank and the storage tank can include a decontamination region containing fuel and an ultraviolet light source located in the decontamination region. Power can be supplied to the pump motor, wherein the pump motor power simultaneously supplies power to the ultraviolet light source. The fuel can then be irradiate with the ultraviolet light.

The ultraviolet light source can be located on top of the fuel in the tank, within the fuel in the tank, on the bottom of the tank, or a combination comprising at least one of the foregoing. The ultraviolet light source can be selected from a light array, a light emitting diode assembly, a drop tube, or a combination comprising at least one of the foregoing. The power source can include direct current, alternating current, or a combination comprising at least one of the foregoing. The alternating current can include a power of 120/240 Volts and the direct current can include a power of 6 Volts. The power source can include a power transformer capable of transforming from alternating current to direct current or from direct current to alternating current at various voltages. The power supply connector can include a pin connector configured to attach the pump motor to the pump head. The pin connector comprises greater than or equal to 1 pin, for example greater than or equal to 2 pins, for example, greater than or equal to 3 pins. The power supply connector can include an adaptor configured to attach the pump motor to the pump head.

A power supply connector for connecting a submersible pump and a light source, can include a submersible pump disposed within a storage tank and a power supply connector attached to the submersible pump, where the power supply connector can be dispersed between a pump motor and a pump head or the power supply connector can be dispersed above the pump head. The power supply connector can include a pin connector configured to attach the pump motor to the pump head. The power supply connector can include an adaptor configured to attach the pump motor to the pump head. The power source can include direct current, alternating current, or a combination comprising at least one of the foregoing; and the power source can include a power transformer capable of transforming from alternating current to direct current or from direct current to alternating current at various voltages.

A fuel decontamination unit can include a power supply connector attached to a submersible pump dispersed between a pump motor and a pump head or the power supply connector can be dispersed above the pump head. The submersible pump can be located within a storage tank and the storage tank can include a decontamination region containing fuel and an ultraviolet light source located in the decontamination region. The decontamination unit can contain fuel and the ultraviolet light can be configured to irradiate the fuel.

The ultraviolet light source can be located on top of the fuel in the tank, within the fuel in the tank, on a bottom portion of the tank, or a combination comprising at least one of the foregoing. The ultraviolet light can be encapsulated within an ultraviolet light transmissive material such that the ultraviolet light is not in direct contact with the fuel. The ultraviolet light source can be selected from a light array, a light emitting diode assembly, a drop tube, or a combination comprising at least one of the foregoing. The power source can include direct current, alternating current, or a combination comprising at least one of the foregoing. The alternating current can include a power of 120/240 Volts and the direct current includes can include a power of 6 Volts. The power source can include a power transformer capable of transforming from alternating current to direct current or from direct current to alternating current at various voltages. The power supply connector can include a pin connector configured to attach the pump motor to the pump head. The pin connector include greater than or equal to 1 pin, for example, greater than or equal to 2 pins, for example, greater than or equal to 3 pins. The power supply connector can include an adaptor configured to attach the pump motor to the pump head.

The decontamination unit can comprise a decontamination region that can reduce or eliminate the amount of microorganisms such as bacteria of the family Acetobacteraceae, specifically of the genus *Acetobacter, Gluconacetbacter*, and *Gluconabacter*; of the family Lactobacillaceae, specifically of the genus *Lactobacillus*; or a combination of one or more of the foregoing. The decontamination region can reduce or eliminate the amount of microorganisms such as fungi of the family Saccharomycetaceae, specifically of the genus *Zygosaccharomyces*.

The decontamination unit can comprise a decontamination region where an ultraviolet light can expose the fuel to ultraviolet radiation to reduce the amount of microorganisms in the fuel. The ultraviolet light can be a light source that can emit ultraviolet radiation that can reduce or eliminate various minerals, microorganisms (such as bacterial and viral), other contaminants, or a combination comprising one or more of the foregoing. The radiation can be ultraviolet-C radiation. The wavelength of the radiation can be 100 nanometers (nm) to 280 nm, specifically 240 nm to 280 nm, more specifically 254 nm. The ultraviolet light can be, for example, a germicidal ultraviolet lamp.

The overall exposure of ultraviolet radiation can be enough to reduce the amount of one or more types of microorganisms by greater than or equal to 80%, specifically greater than or equal to 90%, more specifically, greater than or equal to 99%. The overall exposure of ultraviolet radiation can be greater than or equal to 0.6 watt·second/square centimeter ($Ws/cm^2$), more specifically greater than or equal to 0.65 $Ws/cm^2$.

The total ultraviolet radiation exposure dosage is a product of the intensity of the radiation and the time of exposure. Accordingly, in order to increase the amount of ultraviolet radiation, the intensity of the ultraviolet radiation can be increased or the time of exposure can be increased. The exposure time can also be increased by decreasing the flow rate of the fuel through the decontamination region, increasing the length of said region, or by subjecting the fuel to the decontamination region for an amount of time by stopping and starting the fuel flow. Accordingly, the flow of fuel through the decontamination region can be continuous or can be timed such that fuel enters the decontamination region for an amount of time, the flow is stopped, and subsequently started after said amount of time has passed.

The decontamination region can comprise a tube such as a rectangular tube, a cylindrical tube, or the like, where an ultraviolet light transmissive material (also referred to as a transmissive material) can be located around the entire perimeter of the tube or can be located in only a portion of the perimeter. The decontamination region can comprise a decontamination tank, where the tank can comprise a transmissive material. The tank can be made entirely of the transmissive material or the transmissive material can be localized to a region and can be for example, in the form of a window in the tank. The tube and/or the decontamination tank can be free of a transmissive material.

The overall exposure time of the ultraviolet radiation can be in part, a function of the thickness and the ultraviolet transmissivity of a transmissive material that is used in the decontamination region. Accordingly, the transmissive material can be one that has adequate stability in the presence of the UV radiation used herein for a desired period of time. The transmissive material can comprise a fluorocarbon material (such as poly(trifluorochloroethane) for example sold as KEL-F (by Minnesota Mining and manufacturing) or Teflon), quartz, crystal, glass, an organic resin (such as polycarbonate, a silicon rubber, polyvinylidene fluoride, and polyvinyl chloride), or a combination comprising one or more of the foregoing. The transmissive material can be localized to a region that is exposed to ultraviolet radiation.

The decontamination unit can comprise a tube for transporting the fuel to the ultraviolet light source and can optionally comprise a decontamination tank, where the tube and/or the decontamination tank can comprise carbon steel, austenitic stainless steel, ferritic stainless steel, cast iron, brass, cast aluminum alloy, fiberglass, or a combination of one or more of the foregoing. The tube and/or the decontamination tank can comprise a coating that can comprise nickel, epoxy, enamel, varnish rust inhibitors, or lacquer topcoats. The coating can be externally and/or internally located. The tube and/or the decontamination tank can comprise a fiberglass coated steel. If there is a tube in the decontamination region, then the tube for transporting fuel to the decontamination region can be the same as the tube located in the decontamination region.

The inner surface of either a tube or a decontamination tank that comprises the fuel in the decontamination region can be coated with an ultraviolet reflecting material to increase the intensity and maximize the incidence from multiple directions of the ultraviolet light. Such a coating can be especially useful when the light transmissive material is localized to only a region, such as on one half of the tube or to a window in the decontamination tank, and the ultraviolet-reflective material is located on the inside of the surrounding material. Likewise, such a coating can be especially useful if the ultraviolet light is located within the tube or the decontamination tank and the coating is located on the inside of the surrounding tube or on the inside of the decontamination tank.

The decontamination unit can comprise a tube and a decontamination region as illustrated in FIG. 1, where FIG. 1 illustrates a decontamination unit that comprises a tube 4 with an inlet 1 for the fuel to enter a decontamination region 3 and an outlet 2 for fuel to exit the decontamination region 3. The fuel can be fed into the inlet 1 via gravity or can be pumped into the inlet 1.

Figure 2:
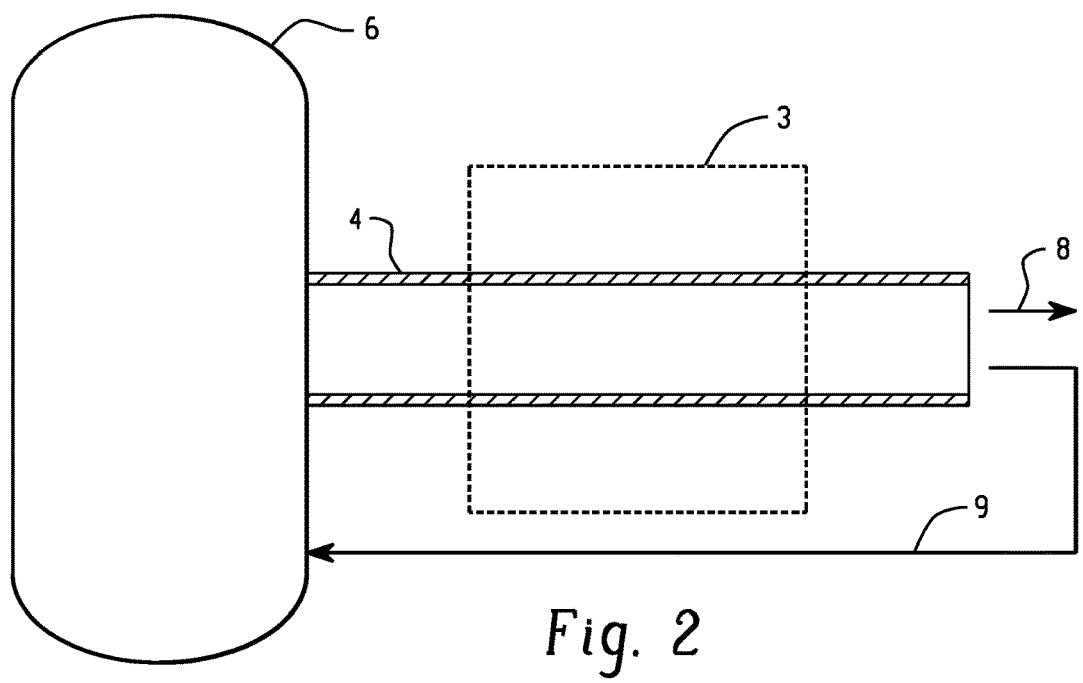
FIG. 2 illustrates a decontamination unit wherein the fuel flows from a storage tank and is either reintroduced to the storage tank or transported elsewhere.

The fuel entering the inlet can originate from a storage tank 6 as illustrated in FIG. 2. The storage tank can be any storage tank such as an above ground storage tank, an in ground storage tank, a gas tank in a vehicle, or the like. The decontaminated fuel that exits the decontamination region 3 can be directed back into the storage tank 6 via path 9 or can be directed to a transport vessel, an engine for use, a different storage vessel, or the like along path 8.

The decontamination region can comprise an ultraviolet light that can be located external to the tube and/or can be internally located such that the fuel surrounds at least a portion of the ultraviolet light.

Figure 3:
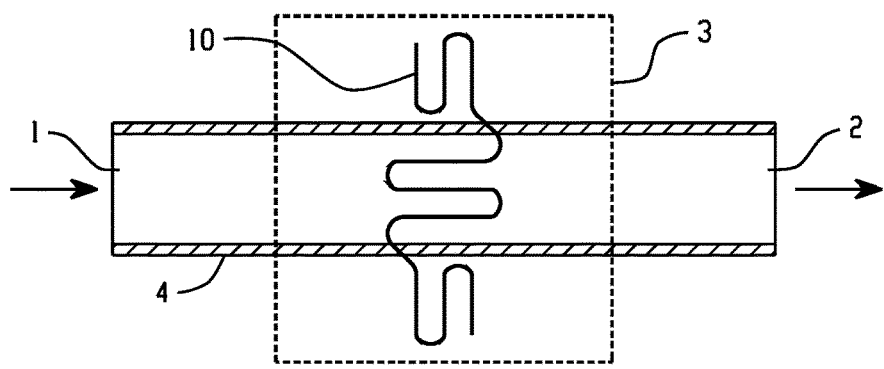
FIG. 3 illustrates a decontamination unit that comprises an externally located ultraviolet light comprising convolutions.

FIG. 3 illustrates that the ultraviolet light can be an ultraviolet light with convolutions 10. The convolutions can be located on one or more sides of the tube 4. There can be any number of convolutions on each side of the tube, where the number of convolutions on each side of the tube can be the same or different.

Figure 4:
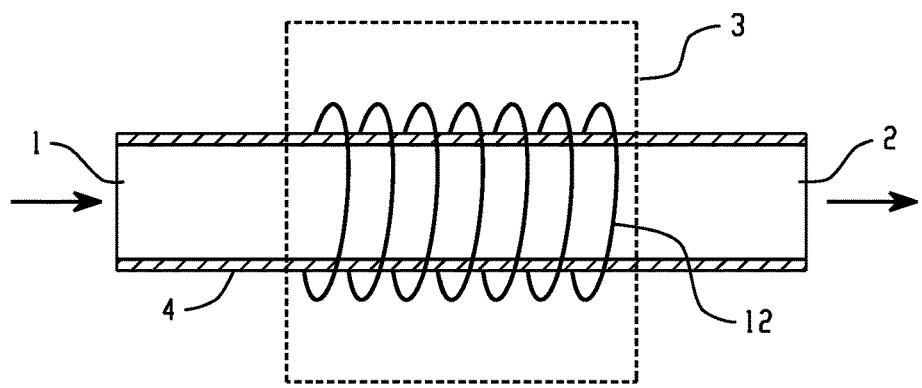
FIG. 4 illustrates a decontamination unit that comprises an externally located ultraviolet light following a helical path around a tube.

FIG. 4 illustrates that the ultraviolet light can be a helical ultraviolet light 12 such that the helical ultraviolet light 12 traverses a helical path with a plurality of turns around the tube 4.

Likewise, the fuel can flow in a tube that is located next to or around (i.e. helically located around) an ultraviolet light. An advantage to having the fuel flow in a tube that travels in a helical path around an ultraviolet light is that it is thereby possible to provide a relatively long contact time between the fuel and the ultraviolet light within a shorter distance.

Figure 5:
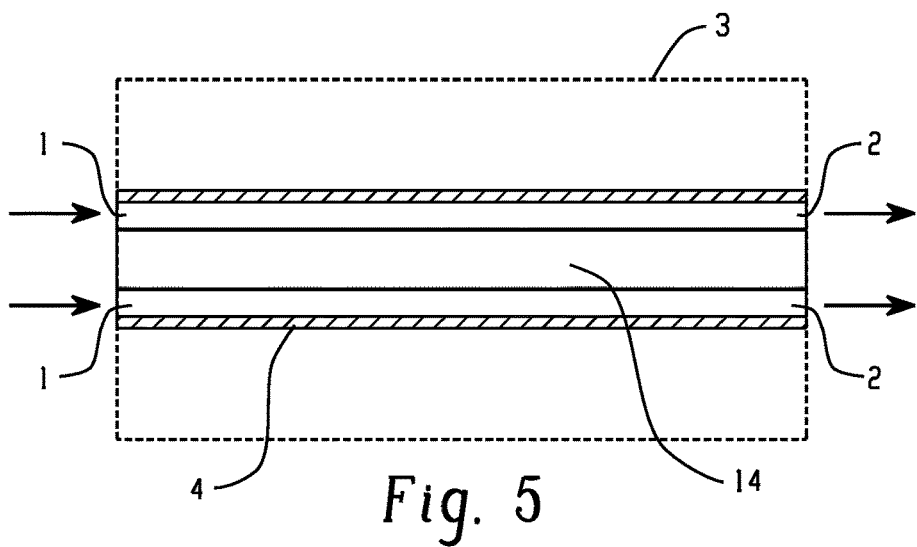
FIG. 5 illustrates a decontamination unit, wherein an ultraviolet light is located co-linearly within a tube.

FIG. 5 illustrates that the ultraviolet light can be a co-linear internal ultraviolet light 14. The co-linear internal ultraviolet light 14 can be located within the tube 4 such that the fuel flows around the ultraviolet light.

Figure 6:
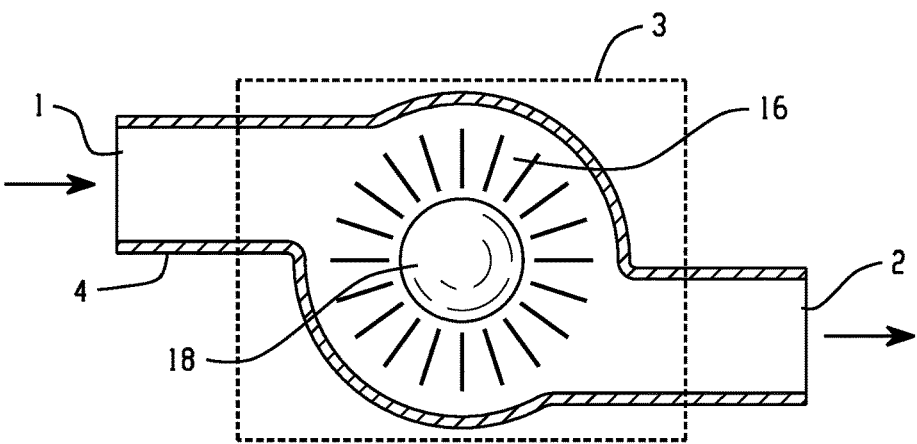
FIG. 6 illustrates a decontamination unit, wherein an ultraviolet light is located within a well region of a tube.

FIG. 6 illustrates that the ultraviolet light can be an internal ultraviolet light 18, where the fuel enters a well region 16 and surrounds the internal ultraviolet light 18. The internal ultraviolet light 18 can be any shape, for example it can be tubular and can comprise helixes or convolutions, it can be straight, it can be somewhat spherical, or the like.

Figure 7:
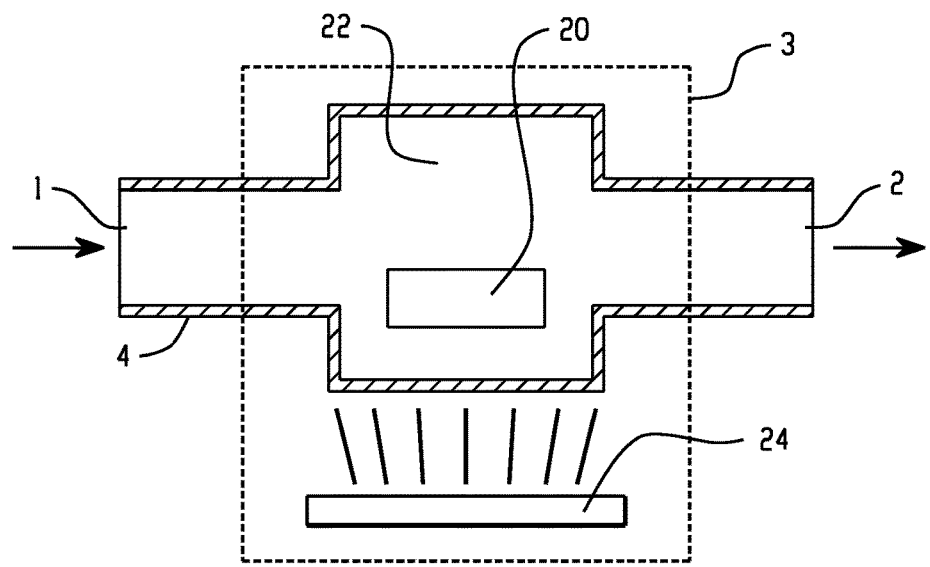
FIG. 7 illustrates a decontamination unit that comprises a decontamination tank.

FIG. 7 illustrates that the decontamination region can comprise a decontamination tank 22, where the fuel enters the decontamination tank 22 through the tube 4. The decontamination tank 22 can be entirely or partially made from an ultraviolet light transmissive material. FIG. 7 illustrates that the decontamination tank 22 can comprise an ultraviolet light transmissive window 20 such that an externally located ultraviolet light 24 can emit ultraviolet radiation through the ultraviolet light transmissive window 20. When a decontamination tank is present, the ultraviolet light can be internally located within the decontamination tank and the decontamination tank can be free of a transmissive material.

Figure 8:
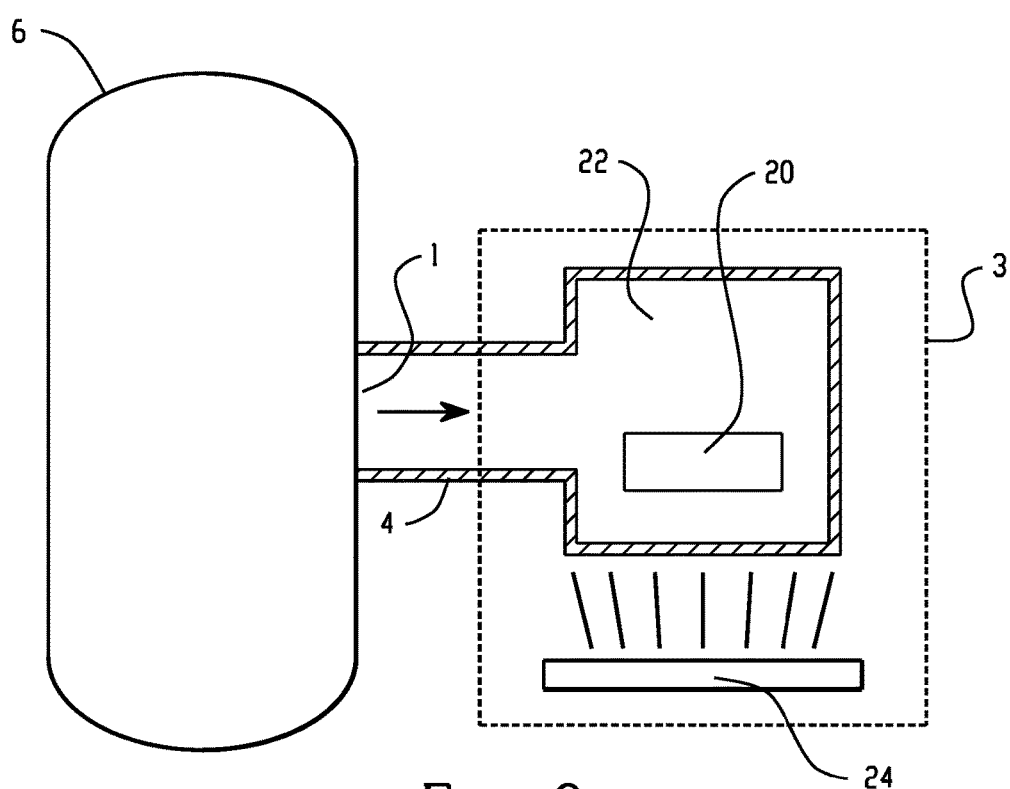
FIG. 8 illustrates a decontamination unit that comprises a decontamination tank, wherein the fuel can traverse through a pipe back and forth from the decontamination tank to a storage tank.

FIG. 8 illustrates that the tube 4 can connect a decontamination tank 22 to a storage tank 6 such that the fuel can naturally diffuse or be actively transported back and forth through the tube 4. In this scenario, although the ultraviolet light 24 only irradiates the fuel in the decontamination tank 22, the fuel in the storage tank 6 is also decontaminated due to the fuel exchange between the two tanks. Instead of being externally located, the ultraviolet light 24 can be located internally within the decontamination tank 22.

Figure 9:
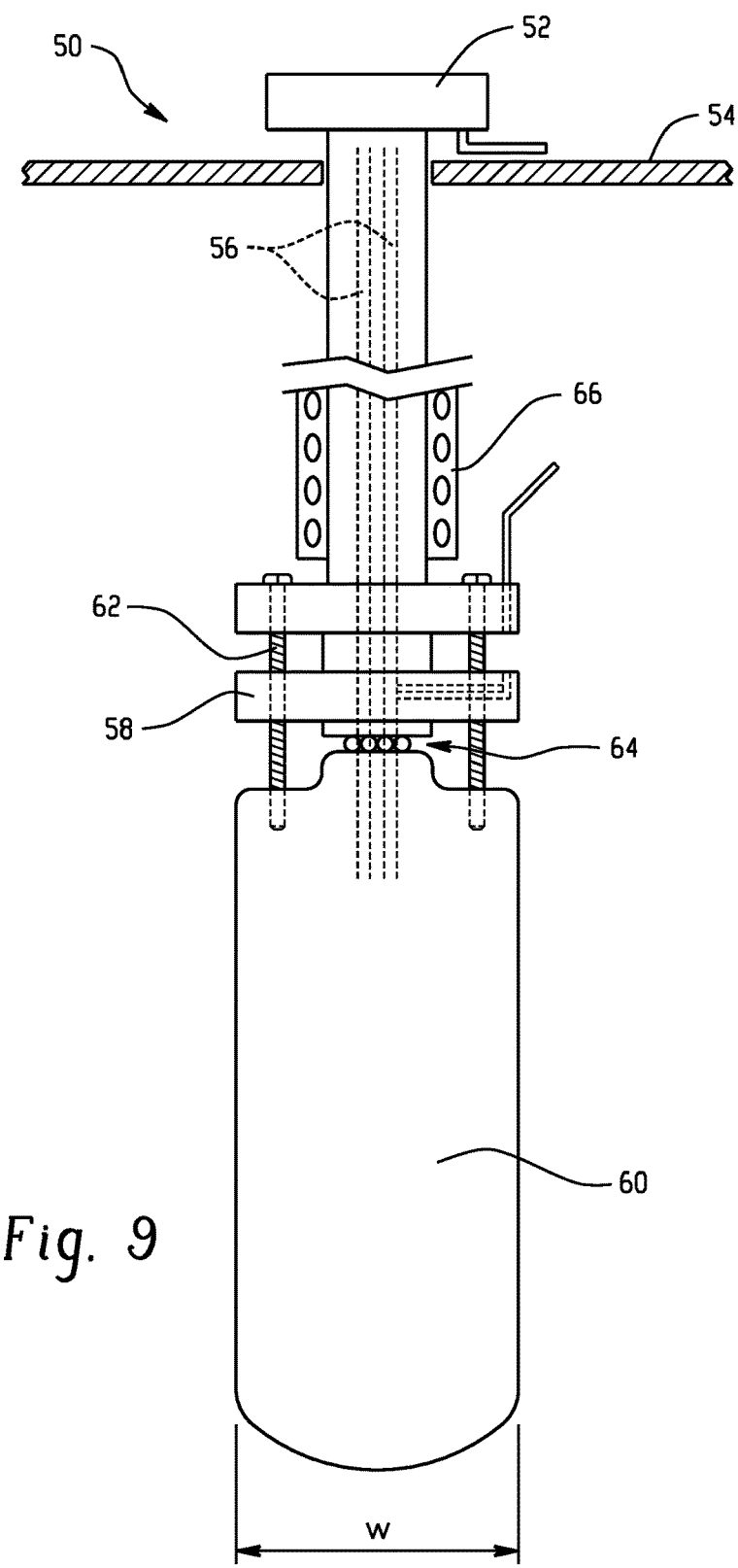
FIG. 9 illustrates a submersible pump with an ultraviolet light source and a power supply connector.

FIG. 9 illustrates a submersible pump and power supply connector assembly 50. A pump head 52 can be located above a tank shell 54 with an electrical supply 56 dispersed within the pump head 52. A light source 66, e.g., a light emitting diode assembly on a drop tub, can be dispersed within the pump and power supply connector assembly 50. The light source 66 can be selected from a light array, a light emitting diode assembly, a drop tube, or a combination comprising at least one of the foregoing. The light source 66 can provide ultraviolet light to the submersible pump and power supply connector assembly 50. A power supply connector 58 can be dispersed between the pump head 52 and a pump motor 60 and connected via a connection mechanism 62 (e.g., bolts, screws, nails, adhesives, etc.). The pump motor 60 can have an overall width, w, of 2 inches to 10 inches, for example, 3 inches to 7 inches, for example, 4 inches. The power supply connector 58 can include a pin 64 that can be configured to attach the pump motor 60 to the pump head 52. There can be greater than or equal to 1 pin, for example, greater than or equal to 2 pins, for example, greater than or equal to 3 pins, for example, greater than or equal to 10 pins. Although described with respect to FIG. 9 in particular locations, it is to be understood that the locations of the various components of the submersible pump and power supply connector assembly 50 can be in a different order than that described. For example, the power supply connector 58 can be located above or below the pump head 52, above or below the light source 66, or between the pin 64 and the pump motor 60.

Figure 10:
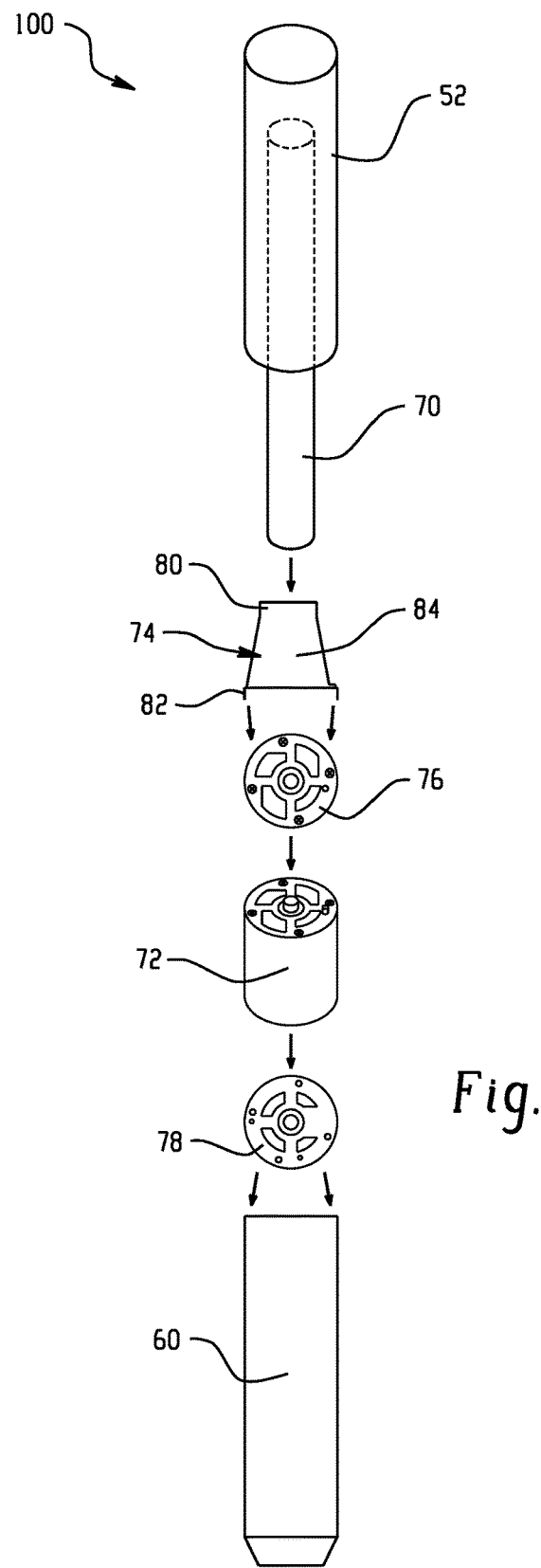
FIG. 10 illustrates a submersible pump with an ultraviolet light source and a power supply connector.

FIG. 10 illustrates a submersible pump and power supply connector assembly 100. In the embodiment shown in FIG. 10, a riser pipe 70 can be located inside of a pump head 52. The riser pipe 70 can have a diameter smaller than a diameter of the pump head 52 to allow the rise pipe 70 to fit within the pump head 52. Disposed below the riser pipe 70 can be a light source adaptor 72 that can include connector housing 74 and a light source filters 76, 78 on a top (light source filter 76) and a bottom (light source filter 78) on a bottom of the light source adaptor 72. Pump motor assembly 60 can be located below the light source adaptor 72. The light source adaptor 72 can be selected from a light array, a light emitting diode assembly, a drop tube, or a combination comprising at least one of the foregoing. The light source can be located within the light source adaptor 72 and can provide ultraviolet light to the submersible pump and power supply connector assembly 100. The pump motor 60 can have an overall width, w, of 2 inches to 10 inches, for example, 3 inches to 7 inches, for example, 4 inches and an overall length of 4 inches to 20 inches, for example, 5 inches to 15 inches, for example, 15 inches.

The light source adaptor 72 can have a constant diameter or can have a varying diameter such that the light source adaptor 72 has a larger or a smaller diameter at a top portion or a bottom portion of the light source adaptor 72. For example, as shown in FIG. 10, the light source adaptor 72 can include a top portion 80 having a smaller diameter than a bottom portion 82, wherein the top portion 80 and the bottom portion 82 are connected by a middle portion 84. The diameter of the top portion 80 and the bottom portion 82 can each, individually, be larger than the diameter of the riser pipe 70 and less than or equal to the diameter of the pump head 52. For example, the diameter of either the top portion 80 or the bottom portion 82 can be less than or equal to 10 inches, for example, less than or equal to 5 inches, for example, less than or equal to 4 inches. A power supply connector can be connected to the submersible pump and power supply connector assembly 100 at any location with the assembly 100. For example, the power supply connector can be located above the pump head 52, below the pump head 52, but above the light source adaptor 72, or below the light source adaptor 72, but above the pump motor assembly 60.

When the power supply connector is located above the pump head 52 in the submersible pump and power supply connector assembly 50, 100, corrosion of the pump head can be limited by allowing for the application of the light source to the pump head. This assists in eliminating the need for a stainless steel pump head.

Although discussed with reference herein to powering the light source, it is to be understood that the power supply connector and adaptor can be used to gather other information from within the tank in which the submersible pump and power supply connector assembly is installed. For example, the power supply connector and adaptor can be used as a transducer to relay information on the contents of the tank, such as density, opacity, temperature, pressure, fluid level, etc. Such measurements can be advantageous for stopping, starting, and/or adjustment of the flow of the light source into the tank.

When the ultraviolet light is externally located, a cooling device such as a fan can further be present and directed on the ultraviolet light to prevent overheating of the light.

The fuel can comprise sulfur in an amount of less than or equal to 15 ppm of sulfur and can optionally comprise an additive. The additive can be an additive for fuel handling (such as those added for de-icing or water removal/encapsulation can comprise alcohols (such as methanol, ethanol, and 1,1'-oxybis-2-propanol) and glycols); fuel stability (such as those composed of strongly basic amines can be added to react with and eliminate weak acids such as acetic acid and formic acid and/or to reduce the amount of microbes); fuel lubricity additives (such as mono- and di-acids or ester synthetic additives); or a combination comprising one or more of the foregoing.

The fuel can comprise low amounts of water. For example, the amount of water that can be present is an amount such that a resultant water layer is less than or equal to 0.25 inches (6.35 millimeters (mm)) deep.

The fuel can comprise low amounts of ethanol. For example, ethanol can be present in an amount of 0 to 5 volume percent, specifically 0 to 1 volume percent, more specifically 0 to 0.2 volume percent, and even more specifically 0 to 0.02 volume percent. Likewise, the fuel can be essentially free of ethanol, where it can comprise 0 to 0.005 volume percent. The amount of ethanol in a water layer, if present, can be greater than or equal to that found in the fuel. For example, the amount of ethanol in the water layer can be 0 to 5 volume percent, specifically 0.04 to 4 volume percent.

Furthermore, in accordance with the disclosed decontamination unit a decontamination method is provided for decontaminating fuel from acetic acid producing microbes in order to potentially reduce or eliminate corrosion of the transport and storage equipment. The method comprises the step of flowing fuel into a decontamination region, wherein ultraviolet light is irradiated onto the fuel in the decontamination region, and flowing the fuel out of the decontamination region.

The methods, connectors, and units disclosed herein include at least the following embodiments:

Embodiment 1: A method of supplying power to a storage tank, comprising: attaching a power supply connector to a submersible, wherein the power supply connector is dispersed between a pump motor and a pump head or wherein the power supply connector is dispersed above the pump head, wherein the submersible pump is located within a storage tank, wherein the storage tank comprises a decontamination region containing fuel and an ultraviolet light source located in the decontamination region; supplying power to the pump motor, wherein the pump motor power simultaneously supplies power to the ultraviolet light source; and irradiating the fuel with the ultraviolet light.

Embodiment 2: The method of Embodiment 1, wherein the ultraviolet light source is located on top of the fuel in the tank, within the fuel in the tank, on the bottom of the tank, or a combination comprising at least one of the foregoing.

Embodiment 3: The method of Embodiment 1 or Embodiment 2, wherein the ultraviolet light source is selected from a light array, a light emitting diode assembly, a drop tube, or a combination comprising at least one of the foregoing.

Embodiment 4: The method of any of Embodiments 1-3, wherein the power source includes direct current, alternating current, or a combination comprising at least one of the foregoing.

Embodiment 5: The method of Embodiment 4, wherein the alternating current includes a power of 120/240 Volts.

Embodiment 6: The method of Embodiment 4, wherein the direct current includes a power of 6 Volts.

Embodiment 7: The method of any of Embodiments 4-6, wherein the power source includes a power transformer capable of transforming from alternating current to direct current or from direct current to alternating current at various voltages.

Embodiment 8: The method of any of Embodiments 1-7, wherein the power supply connector comprises a pin connector configured to attach the pump motor to the pump head or wherein the power supply connector comprises an adaptor configured to attach the pump motor to the pump head.

Embodiment 9: The method of any of Embodiments 1-8, wherein the pin connector comprises greater than or equal to 1 pin.

Embodiment 10: A power supply connector for connecting a submersible pump and a light source, comprising: a submersible pump disposed within a storage tank; and a power supply connector attached to a submersible pump wherein the power supply connector is dispersed between a pump motor and a pump head or wherein the power supply connector is dispersed above the pump head, wherein the power supply connector comprises a pin connector configured to attach the pump motor to the pump head or wherein the power supply connector comprises an adaptor configured to attach the pump motor to the pump head; wherein the power source includes direct current, alternating current, or a combination comprising at least one of the foregoing; and wherein the power source includes a power transformer capable of transforming from alternating current to direct current or from direct current to alternating current at various voltages.

Embodiment 11: The power supply connector of Embodiment 10, wherein the alternating current includes a power of 120/240 Volts.

Embodiment 12: The power supply connector of Embodiment 10, wherein the direct current includes a power of 6 Volts.

Embodiment 13: The power supply connector of any of Embodiments 10-12, wherein the pin connector comprises greater than or equal to 1 pin.

Embodiment 14: A fuel decontamination unit, comprising: a power supply connector attached to a submersible pump wherein the power supply connector is dispersed between a pump motor and a pump head or wherein the power supply connector is dispersed above the pump head, wherein the submersible pump is located within a storage tank, wherein the storage tank comprises a decontamination region containing fuel and an ultraviolet light source located in the decontamination region; wherein the decontamination unit contains fuel and wherein the ultraviolet light is configured to irradiate the fuel.

Embodiment 15: The fuel decontamination unit of Embodiment 14, wherein the ultraviolet light source is located on top of the fuel in the tank, within the fuel in the tank, on a bottom portion of the tank, or a combination comprising at least one of the foregoing.

Embodiment 16: The decontamination unit of Embodiment 14 or Embodiment 15, wherein the ultraviolet light is encapsulated within an ultraviolet light transmissive material such that the ultraviolet light is not in direct contact with the fuel.

Embodiment 17: The fuel decontamination unit of any of Embodiments 14-16, wherein the ultraviolet light source is selected from a light array, a light emitting diode assembly, a drop tube, or a combination comprising at least one of the foregoing.

Embodiment 18: The fuel decontamination unit of any of Embodiments 14-17, wherein the power source includes direct current, alternating current, or a combination comprising at least one of the foregoing.

Embodiment 19: The fuel decontamination unit of Embodiment 18, wherein the alternating current includes a power of 120/240 Volts.

Embodiment 20: The fuel decontamination unit of Embodiment 18, wherein the direct current includes a power of 6 Volts.

Embodiment 21: The fuel decontamination unit of any of Embodiments 14-20, wherein the power source includes a power transformer capable of transforming from alternating current to direct current or from direct current to alternating current at various voltages.

Embodiment 22: The fuel decontamination unit of any of Embodiments 14-21, wherein the power supply connector comprises a pin connector configured to attach the pump motor to the pump head or wherein the power supply connector comprises an adaptor configured to attach the pump motor to the pump head.

Embodiment 23: The fuel decontamination unit of any of Embodiments 14-22, wherein the pin connector comprises greater than or equal to 1 pin.

Embodiment 24: The fuel decontamination unit of any of Embodiments 14-23, wherein the ultraviolet light has a wavelength of 100 nm to 280 nm.

Embodiment 25: The fuel decontamination unit of any of Embodiments 14-24, wherein an amount of microorganisms in the fuel after irradiation is reduced by greater than or equal to 90% as compared to that of contaminated fuel.

Embodiment 26: The fuel decontamination unit of any of Embodiments 14-25, wherein the fuel continuously flows through the decontamination region or wherein the fuel does not continuously flow through the decontamination region.

Embodiment 27: The fuel decontamination unit of any Embodiment 14-25, further comprising a tube comprising the ultraviolet light transmissive material, wherein the ultraviolet light comprises a number of convolutions and wherein the convolutions are located on one or more sides of the tube.

Embodiment 28: The fuel decontamination unit of Embodiment 27, wherein the ultraviolet light is a helical ultraviolet light such that the helical ultraviolet light traverses a helical path with a plurality of turns around the tube.

Embodiment 29: The fuel decontamination unit of Embodiment 28, wherein the tube is a helical tube, wherein the helical tube traverses a helical path with a plurality of turns around the ultraviolet light.

Embodiment 30: The fuel decontamination unit of any of Embodiments 14-29, further comprising a decontamination tank.

Embodiment 31: The fuel decontamination unit of Embodiment 30, further comprising a storage tank and a tube, wherein the fuel enters the decontamination region from the storage tank via the tube and does not re-enter the storage tank or wherein the fuel can traverse back and forth from the decontamination tank to the storage tank via the tube.

Embodiment 32: The fuel decontamination unit of Embodiment 31, wherein the ultraviolet light is located within the decontamination tank.

Embodiment 33: The fuel decontamination unit of Embodiment 32, wherein the decontamination tank comprises an ultraviolet light transmissive material and the ultraviolet light is located proximal to the decontamination unit such that the ultraviolet light irradiates through the ultraviolet light transmissive material.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 volume percent or, more specifically, 5 volume percent to 20 volume percent", is inclusive of the endpoints and all intermediate values of the ranges of "5 volume percent to 25 volume percent," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

With respect to the figures, it is noted that these figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the description for the sake of clarity, these terms are intended to refer only to the particular structure of the embodiments selected for illustration in the drawings, and are not intended to define or limit the scope of the disclosure. In the drawings and the description herein, it is to be understood that like numeric designations refer to components of like function.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

I claim:

1. A method of supplying power to a storage tank, comprising:
   attaching a power supply connector to a submersible pump, wherein the power supply connector is dispersed between a pump motor and a pump head or wherein the power supply connector is dispersed above the pump head, wherein the submersible pump is located within the storage tank, wherein the storage tank comprises a decontamination region containing fuel and an ultraviolet light source located in the decontamination region, wherein the decontamination region further comprises a decontamination tank and a tube, wherein the fuel enters the decontamination region from the storage tank via the tube and does not re-enter the storage tank or wherein the fuel can traverse back and forth from the decontamination region to the storage tank via the tube, wherein an inner surface of the decontamination tank is coated with an ultraviolet reflecting material;
   supplying power to the pump motor, wherein the pump motor power simultaneously supplies power to the ultraviolet light source; and
   irradiating the fuel with the ultraviolet light;
   wherein the storage tank is configured to dispense, transport or store fuel.

2. The method of claim 1, wherein the ultraviolet light source is located on top of the fuel in the tank, within the fuel in the tank, on the bottom of the tank, or a combination comprising at least one of the foregoing.

3. A power supply connector for connecting a submersible pump and a light source, comprising:
   the submersible pump disposed within a storage tank, wherein the storage tank is configured to dispense, transport or store fuel; and
   the power supply connector attached to the submersible pump wherein the power supply connector is dispersed between a pump motor and a pump head or wherein the power supply connector is dispersed above the pump head, wherein the power supply connector comprises a pin connector configured to attach the pump motor to the pump head or wherein the power supply connector comprises an adaptor configured to attach the pump motor to the pump head, wherein the storage tank comprises a decontamination unit containing fuel and an ultraviolet light source located in the decontamination unit, wherein the ultraviolet light source is configured to irradiate the fuel; wherein the decontamination unit further comprises a decontamination tank and a tube, wherein the fuel enters the decontamination tank from the storage tank via the tube and does not re-enter the storage tank or wherein the fuel can traverse back and forth from the decontamination tank to the storage tank via the tube, wherein an inner surface of the decontamination tank is coated with an ultraviolet reflecting material;
   wherein the power source includes direct current, alternating current, or a combination comprising at least one of the foregoing; and
   wherein the power source includes a power transformer capable of transforming from alternating current to direct current or from direct current to alternating current at various voltages.

4. The power supply connector of claim 3, wherein the alternating current includes a power of 120/240 Volts and wherein the direct current includes a power of 6 Volts.

5. A fuel decontamination unit, comprising:
a power supply connector attached to a submersible pump wherein the power supply connector is dispersed between a pump motor and a pump head or wherein the power supply connector is dispersed above the pump head, wherein the submersible pump is located within a storage tank, wherein the storage tank comprises a decontamination region containing fuel and an ultraviolet light source located in the decontamination region;
wherein the decontamination unit contains fuel and wherein the ultraviolet light is configured to irradiate the fuel;
wherein the storage tank is configured to dispense, transport or store fuel;
wherein the fuel decontamination unit further comprises a decontamination tank and a tube, wherein the fuel enters the decontamination region from the storage tank via the tube and does not re-enter the storage tank or wherein the fuel can traverse back and forth from the decontamination tank to the storage tank via the tube, wherein an inner surface of the decontamination tank is coated with an ultraviolet reflecting material.

6. The fuel decontamination unit of claim 5, wherein the ultraviolet light source is located on top of the fuel in the tank, within the fuel in the tank, on a bottom portion of the tank, or a combination comprising at least one of the foregoing.

7. The decontamination unit of claim 5, wherein the ultraviolet light is encapsulated within an ultraviolet light transmissive material such that the ultraviolet light is not in direct contact with the fuel.

8. The fuel decontamination unit of claim 5, wherein the ultraviolet light source is selected from a light array, a light emitting diode assembly, a drop tube, or a combination comprising at least one of the foregoing.

9. The fuel decontamination unit of claim 5, wherein the power supply connector comprises a power source including direct current, alternating current, or a combination comprising at least one of the foregoing.

10. The fuel decontamination unit of claim 9, wherein the alternating current includes a power of 120/240 Volts and wherein the direct current includes a power of 6 Volts.

11. The fuel decontamination unit of claim 5, wherein the power source includes a power transformer capable of transforming from alternating current to direct current or from direct current to alternating current at various voltages.

12. The fuel decontamination unit of claim 5, wherein the ultraviolet light has a wavelength of 100 nm to 280 nm.

13. The fuel decontamination unit of claim 5, wherein an amount of microorganisms in the fuel after irradiation is reduced by greater than or equal to 90% as compared to that of contaminated fuel.

14. The fuel decontamination unit of claim 5, wherein the fuel continuously flows through the decontamination region or wherein the fuel does not continuously flow through the decontamination region.

15. The fuel decontamination unit of claim 5, further comprising a tube comprising the ultraviolet light, wherein the ultraviolet light comprises a number of convolutions and wherein the convolutions are located on one or more sides of the tube.

16. The fuel decontamination unit of claim 15, wherein the ultraviolet light is a helical ultraviolet light such that the helical ultraviolet light traverses a helical path with a plurality of turns around the tube.

17. The fuel decontamination unit of claim 16, wherein the tube is a helical tube, wherein the helical tube traverses a helical path with a plurality of turns around the ultraviolet light.

18. The fuel decontamination unit of claim 5, wherein the decontamination tank comprises carbon steel, austenitic stainless steel, ferritic stainless steel, cast iron, brass, cast aluminum alloy, fiberglass, or a combination of one or more of the foregoing.

* * * * *